(12) United States Patent
Paul

(10) Patent No.: US 8,803,522 B2
(45) Date of Patent: Aug. 12, 2014

(54) METHOD AND MAGNETIC RESONANCE SYSTEM TO ACQUIRE MR DATA IN A PREDEFINED THREE-DIMENSIONAL VOLUME SEGMENT

(75) Inventor: Dominik Paul, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 408 days.

(21) Appl. No.: 13/297,509

(22) Filed: Nov. 16, 2011

(65) Prior Publication Data

US 2012/0126813 A1 May 24, 2012

(30) Foreign Application Priority Data

Nov. 16, 2010 (DE) .......................... 10 2010 043 956

(51) Int. Cl.
*G01V 3/00* (2006.01)

(52) U.S. Cl.
USPC ........................................................ 324/309

(58) Field of Classification Search
USPC ................................................ 324/300–322
See application file for complete search history.

(56) References Cited

U.S. PATENT DOCUMENTS

| 5,134,372 A | 7/1992 | Inoue |
| 5,528,145 A * | 6/1996 | Hirata et al. .................. 324/309 |
| 6,377,048 B1 * | 4/2002 | Golan et al. .................. 324/318 |
| 6,704,594 B1 * | 3/2004 | Blank et al. .................... 600/423 |
| 7,109,709 B2 | 9/2006 | Asano |
| 2003/0003053 A1 | 1/2003 | Uetake |
| 2013/0249550 A1 * | 9/2013 | Feiweier et al. .............. 324/309 |

OTHER PUBLICATIONS

"Handbook of MRI Pulse Sequences," Bernstein et al. (2004) p. 598.
"¹H NMR Chemical Shift Selective (CHESS) Imaging," Haase et al., Phys. Med. Biol., vol. 30, No. 4 (1985) pp. 341-344.

* cited by examiner

*Primary Examiner* — Dixomara Vargas
(74) *Attorney, Agent, or Firm* — Schiff Hardin LLP

(57) ABSTRACT

In a method and magnetic resonance (MR) apparatus to acquire MR data in a predetermined three-dimensional volume segment of an examination subject, the three-dimensional volume segment is selectively excited with an RF excitation pulse, wherein a magnetic field gradient at the same time is switched. Two phase coding gradients and an additional magnetic field gradient are switched for spatial coding and MR data are acquired depending on this. A frequency range of the RF excitation pulse is set depending on resonance frequencies of at least two substances to be acquired within the volume segment, such that a center frequency of the frequency range is caused to be located between the resonance frequencies.

11 Claims, 6 Drawing Sheets

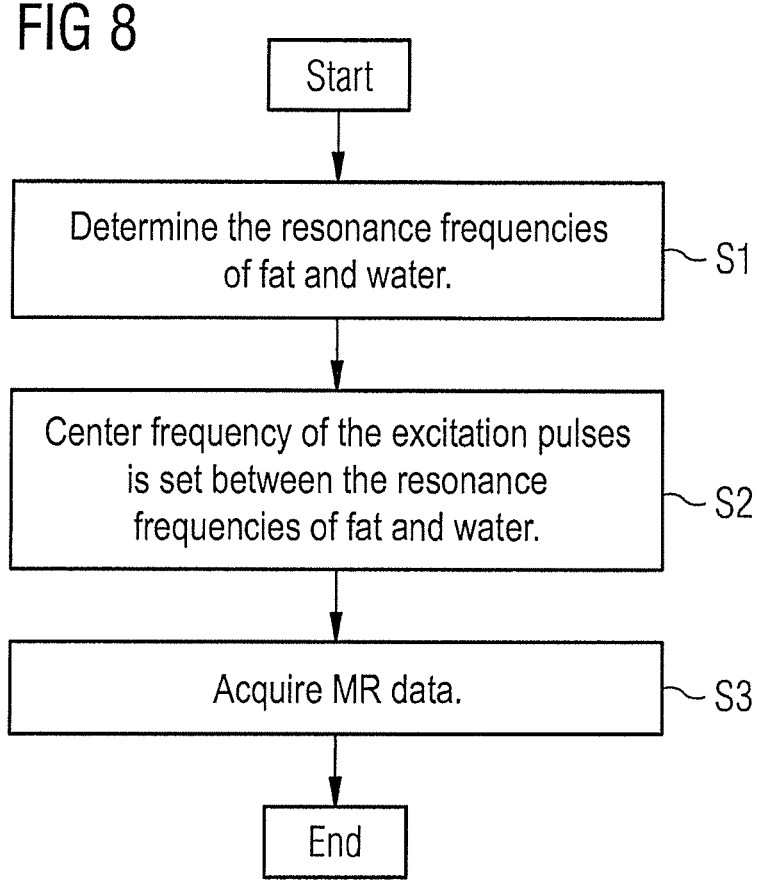

METHOD AND MAGNETIC RESONANCE SYSTEM TO ACQUIRE MR DATA IN A PREDEFINED THREE-DIMENSIONAL VOLUME SEGMENT

BACKGROUND OF THE INVENTION

1. Field of the Invention

The present invention concerns a method in order to acquire MR data in a predefined three-dimensional volume segment while avoiding aliasing and banding artifacts, as well as a correspondingly designed magnetic resonance system.

2. Description of the Prior Art

For example, in the SPACE method ("Sampling Perfection with Application optimized Contrasts using different flip angle Evolutions"), which operates with a selective excitation, artifacts occur due to the chemical shift between different chemical structures (for example fat and water), which artifacts degrade the diagnostic significance of the generated MR images, dark regions ("dark bands") occur in the direction of the basic magnetic field on the one side of the three-dimensional volume segment to be acquired, and on the other hand MR signals in the volume segment are aliased on the other side of adipose tissue situated outside of said volume segment. The reason for the two artifact types lies in the occurring chemical shift, which can affect a majority of the MR image.

SUMMARY OF THE INVENTION

An object of the present invention is to attenuate the effects of the artifacts caused by a chemical shift.

A method in accordance with the invention to acquire MR data in a predetermined three-dimensional volume segment of an examination subject by means of a magnetic resonance system includes the following steps.

The three-dimensional volume segment is selectively excited with an RF excitation pulse, wherein a magnetic field gradient is switched at the same time. The frequency range of this RF excitation pulse is set depending on resonance frequencies of two or more substances within the volume segment that are to be detected via the method according to the invention, such that a center frequency of the frequency range is arranged between these resonance frequencies.

Two phase coding gradients and an additional magnetic field gradient are switched for spatial coding.

The MR data are acquired.

Each substance has its own resonance frequency depending on the type of chemical bond in which the respective atomic nuclei are located and proportional to the magnetic field strength. In that the center frequency of the frequency range of the RF excitation pulse is arranged between the resonance frequencies for the substances to be acquired, which resonance frequencies are applicable for the corresponding strength of the basic magnetic field, the atomic nuclei of the various substances are more suitably excited than if the center frequency corresponds to the resonance frequency of water, as is the case according to the prior art. This is explained in more detail in the following.

As used herein the center frequency means the frequency that lies in the middle of the frequency range of the RF excitation pulse.

For example, the center frequency can be set to the average of the resonance frequencies of the substances to be detected, wherein the average can be an arithmetic mean, geometric mean or the median.

For example, if the substances to be detected are water and fat and the center frequency corresponds to the average of the resonance frequency of water and the resonance frequency of fat, the protons (H atoms) of aqueous tissue and the protons of fat in the target volume (i.e. in the predetermined volume segment) are excited just as well as is explained in detail in the following with reference to Figures. The artifacts caused by the adipose tissue can thereby advantageously be at least reduced relative to the prior art.

In comparison to the prior art, the frequency range of the RF excitation pulse according to the present invention is shifted depending on the substances to be detected (more precisely, depending on the respective resonance frequencies of the substances to be detected). A respective volume segment, which normally does not correspond to the predetermined volume segment, is thereby excited by the same RF excitation pulse for each of the substances to be detected. (According to the invention, the single exception to the rule just described then exists if more than two substances are to be detected and the center frequency corresponds precisely to a resonance frequency of these substances.) In spite of this, the predetermined volume segment is read out upon acquisition of the MR data. This means that the three-dimensional spatial coding for acquisition of the MR data takes place such that the predetermined volume segment is read out.

In a preferred embodiment according to the invention, the strength of the magnetic field gradient which is switched for selection during the RF excitation pulse is decreased such that a respective border region before and after (in the direction of this magnetic field gradient) the volume segment excited with regard to the respective substance are excited and MR data are acquired in these border regions.

By increasing the excited volume, the corresponding substances are now also advantageously excited at the edge within the predetermined volume segment, which corresponding substances are not excited without this decrease [sic] due to their resonance frequency offset from the center frequency. Via this procedure, the dark regions which are caused by unexcited substances within the target volume are accordingly at least reduced.

In an additional embodiment according to the invention, MR data in border regions before and after (in the direction of the magnetic field gradient) the volume segment are also acquired by means of an oversampling.

By oversampling, the volume in which MR data are acquired is larger than the predetermined volume segment. Since the artifacts caused by aliasing occur at the edge of the acquired volume, the aliasing can thereby be virtually shifted out of the predetermined volume segment. To create an MR image data set of the predetermined volume segment, the part corresponding to the predetermined volume segment is extracted from the MR image data set of the scanned volume. Expressed differently, an MR image data set of the volume is created starting from the MR data which are acquired from the scanned volume. This MR image data set has aliasing artifacts at the edge. Since the predetermined volume segment is smaller than this volume, the MR image data set of the volume segment corresponds only to a portion of the MR image data set of the volume. If the oversampling is set so that the aliasing pertains only to that part of the MR image data set of the volume which does not belong to the MR image data set of the predetermined volume segment, the MR image data set of the predetermined volume segment can be created from the MR image data set of the volume without said MR image data sets having aliasing artifacts.

In the normal case, the magnetic field gradient which is switched simultaneously with the RF excitation pulse travels in the direction of the basic magnetic field of the magnetic resonance system. Moreover, a first of the two phase coding gradients likewise travels in the direction of this basic magnetic field while the second phase coding gradient is situated perpendicular to the first phase coding gradient, and therefore also perpendicular to the direction of the basic magnetic field. The additional magnetic field gradient (which is in particular used for frequency coding) is now situated perpendicular to both the first and the second phase coding gradient.

While the acquisition of the MR data within a Cartesian coordinate system is described in the preceding, it is noted that the acquisition of the MR data (by switching the phase coding gradient and the additional magnetic field gradient) can take place in an arbitrary form so that the method according to the invention can also operate with spherical coordinates or cylindrical coordinates to acquire the MR data, for example.

If the additional magnetic field gradient is used for frequency coding, a k-space line (256 points, for example) in the direction of this additional magnetic field gradient can advantageously be read out in one step.

According to the invention, refocusing pulses can be used for refocusing the spins. These refocusing pulses can thereby be developed selectively or non-selectively. In the event that selective refocusing pulses are used, it is reasonable if the frequency range of the refocusing pulses corresponds to the frequency range of the RF excitation pulse.

Within the scope of the present invention, a magnetic resonance system is also provided to acquire MR data of a predetermined three-dimensional volume segment within an examination subject. The magnetic resonance system has a basic field magnet; a gradient field system; one or more RF antennas; and a control device to activate the gradient field system and the RF antenna(s), to receive the measurement signals which are acquired by the RF antenna(s), and to evaluate the measurement signals and create the MR image data sets. The magnetic resonance system selectively excites the three-dimensional volume segment with an RF excitation pulse, wherein a magnetic field gradient is switched at the same time. The frequency range of the RF excitation pulse is thereby set by the magnetic resonance system depending on resonance frequencies which have two or more substances within the volume segment, such that a center frequency of this frequency range lies between these resonance frequencies. In order to acquire the MR data within the volume segment, the magnetic resonance system switches two phase coding gradients and an additional magnetic field gradient for spatial coding.

The advantages of the magnetic resonance system according to the invention substantially correspond to the advantages of the method according to the invention described in detail above.

Furthermore, the present invention also encompasses a non-transitory, computer-readable data storage medium encoded with programming instructions/control commands (in particular a software) that can be loaded into a memory of a programmable control device or a computer of a magnetic resonance system. All or various embodiments of the method according to the invention that are described in the preceding can be executed when the control device executes the programming instructions. The programming instructions may require program means, for example libraries and auxiliary functions in order to realize corresponding embodiments of the method. The programming instructions can be source code (C++, for example) that must still be compiled and linked or must only be interpreted, or can be in the form of an executable software code that has only to be loaded into the corresponding computer or control device for execution.

The electronically readable data storage medium can be, for example, a DVD, a magnetic tape or a USB stick on which is stored electronically readable control information, in particular software (see above).

The present invention is particularly suitable to acquire MR data in a three-dimensional volume segment in order to generate an image data set of the volume segment based on these MR data. Naturally, the present invention is not limited to this preferred field of application since the present invention can also be used to create spatially dependent spectral information within the volume segment, for example.

BRIEF DESCRIPTION OF THE DRAWINGS

FIG. 8 is a flow chart of an embodiment of the method according to the invention.

DESCRIPTION OF THE PREFERRED EMBODIMENTS

Figure 1:
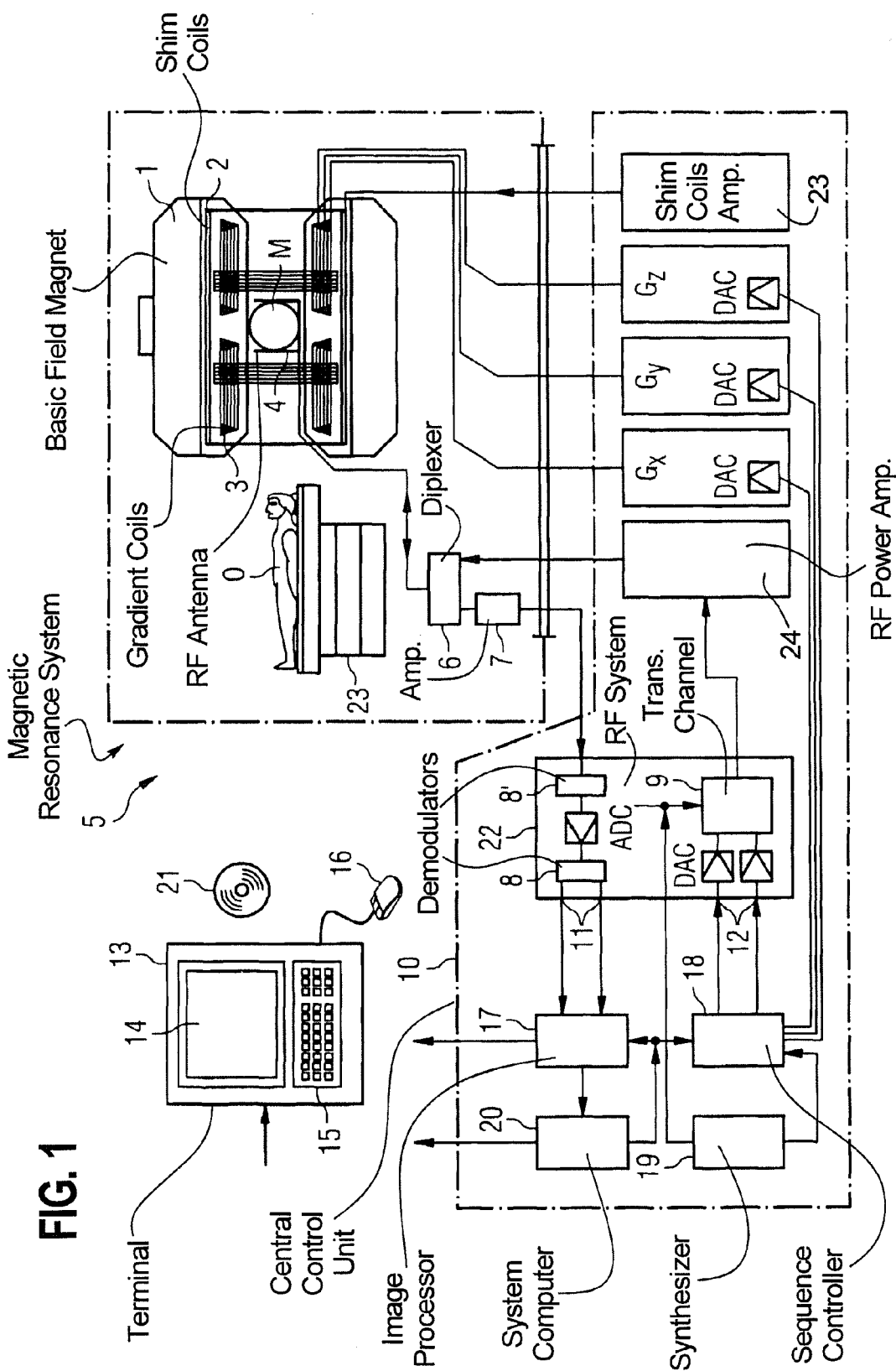
FIG. 1 shows a magnetic resonance system according to the invention.

FIG. 1 is a schematic representation of a magnetic resonance system 5 (a magnetic resonance imaging or magnetic resonance tomography apparatus). A basic field 1 magnet generates a temporally constant, strong magnetic field for polarization or, respectively, alignment of the nuclear spins in a volume segment of a subject O, for example a part of a human body that is to be examined, which body (lying on a table 23) is examined in the magnetic resonance system 5. The high homogeneity of the basic magnetic field that is required for nuclear magnetic resonance measurement is defined in a typically spherical measurement volume M in which the parts of the human body that are to be examined are arranged. Components are known as shim plates made of ferromagnetic material are attached at suitable points to assist the homogeneity requirements, and in particular to eliminate temporally invariable influences. Temporally variable influences are eliminated by shim coils 2 that are operated by a shim coils amplifier 23.

A cylindrical gradient coil system 3 composed of three sub-windings is used in the basic field magnet 1. Each sub-winding is supplied with current by an amplifier to generate a linear (and temporally variable) gradient field in the respective direction of the Cartesian coordinate system. The first sub-winding of the gradient field system 3 thereby generates a gradient $G_x$ in the x-direction; the second sub-winding generates a gradient $G_y$ in the y-direction; and the third sub-winding generates a gradient $G_z$ in the z-direction. Each amplifier includes a digital/analog converter that is activated by a sequence controller 18 for accurately-timed generation of gradient pulses.

One or more radio-frequency antennas 4 which convert the radio-frequency pulses emitted by a radio-frequency power amplifier 24 into an alternating magnetic field for excitation of the nuclei and alignment of the nuclear spins of the subject O to be examined or, respectively, of the region of the subject O that is to be examined is located within the gradient field system 3. Each radio-frequency antenna 4 consists of one or more RF transmission coils and one or more RF reception coils in the form of an annular, advantageously linear, or matrix-like arrangement of component coils. The alternating field emanating from the precessing nuclear spins—i.e. normally the nuclear spin echo signals caused by a pulse sequence made up of one or more radio-frequency pulses and one or more gradient pulses—is also converted by the RF reception coils into a voltage (measurement signal) which is supplied via an amplifier 7 to a radio-frequency reception channel 8 of a radio-frequency system 22. The radio-frequency system 22 furthermore has a transmission channel 9 in which the radio-frequency pulses are generated for the excitation of the nuclear magnetic resonance. The respective radio-frequency pulses are thereby digitally represented in the sequence controller 18 as a series of complex numbers based on a pulse sequence predetermined by the system computer 20. This number sequence is supplied as a real part and imaginary part to a digital/analog converter in the radio-frequency system 22 via a respective input 12 and from said digital/analog converter (DAC) to a transmission channel 9. In the transmission channel 9 the pulse sequences are modulated on a radio-frequency carrier signal whose base frequency corresponds to the center frequency.

The switching from transmission operation to reception operation takes place via a transmission/reception diplexer 6. The RF transmission coils of the radio-frequency antenna(s) 4 radiate(s) the radio-frequency pulses for excitation of the nuclear spins into the measurement volume M, and resulting echo signals are scanned via the RF reception coil(s). The correspondingly acquired magnetic resonance signals are phase-sensitively demodulated on an intermediate frequency in an acquisition channel 8' (first demodulator) of the radio-frequency system 22 of the radio-frequency system 22 and digitized in an analog/digital converter (ADC). This signal is further demodulated on a frequency of 0. The demodulation on a frequency of 0 and the separation into real part and imaginary part occurs in a second demodulator 8 after the digitization in the digital domain. An MR image or three-dimensional image data set is reconstructed by the image computer 17 from the measurement data acquired in such a manner. The administration of the measurement data, the image data and the control programs takes place via the system computer 20. Based on a specification with control programs, the sequence controller 18 monitors the generation of the respective desired pulse sequences and the corresponding scanning of k-space. In particular, the sequence controller 18 thereby controls the time-accurate switching of the gradients, the emission of the radio-frequency pulses with defined phase amplitude and the reception of the magnetic resonance signals. The time base for the radio-frequency system 22 and the sequence controller 18 is provided by a synthesizer 19. The selection of corresponding control programs (stored on a DVD 21, for example) to generate an MR image and the presentation of the generated MR image take place via a terminal 13 that has a keyboard 15, a mouse 16 and a monitor 14.

Figure 2:
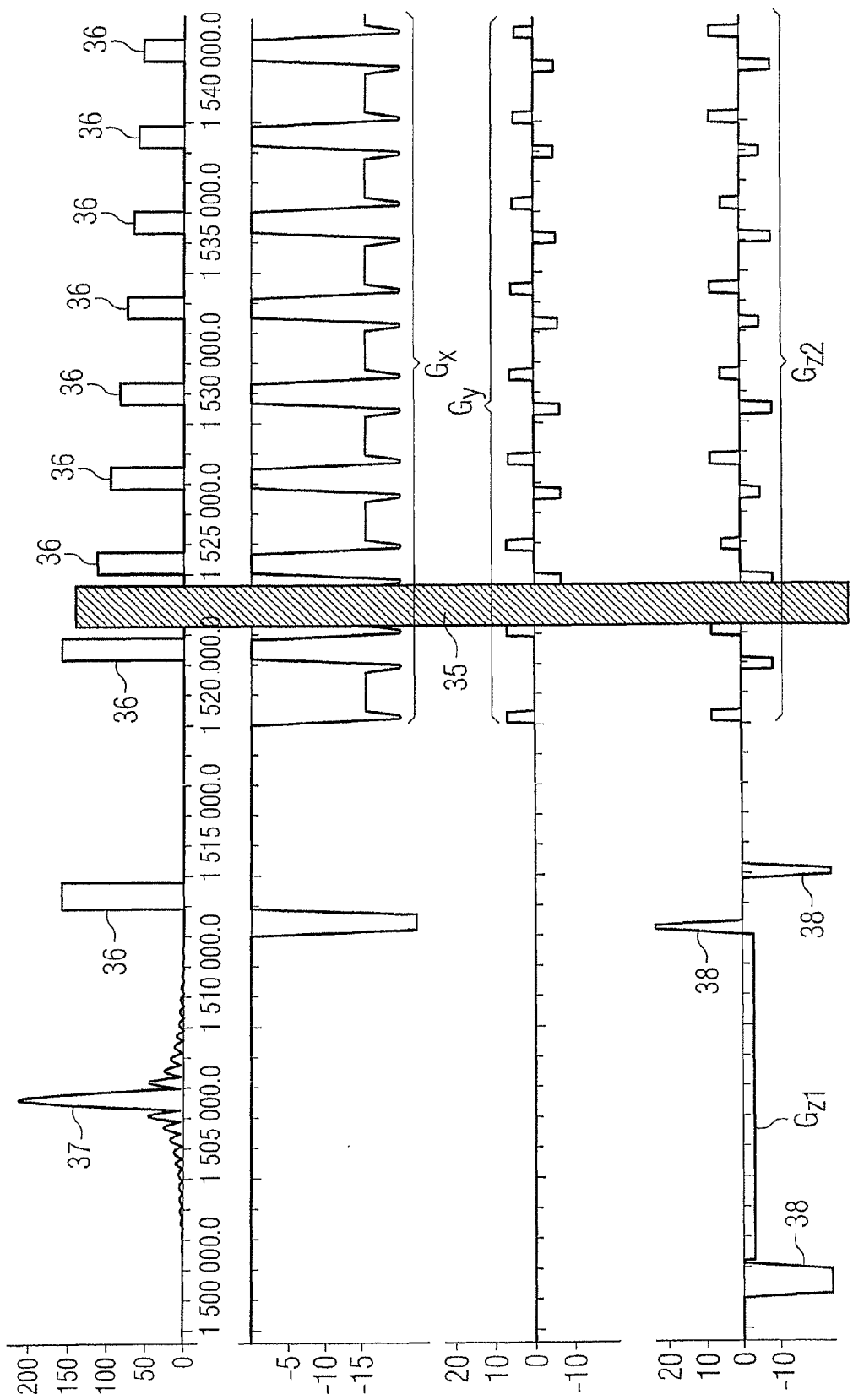
FIG. 2 shows a gradient pulse sequence according to the invention for acquisition of MR data within a three-dimensional volume segment.

A pulse sequence according to the invention is shown in FIG. 2. After a spoiler gradient 38 to destroy "old" magnetization, an RF excitation pulse 37 is switched together with a magnetic field gradient $G_{z1}$ in order to excite the spins within the predetermined volume segment. The center frequency of the frequency range of this RF excitation pulse 37 lies in the center of the resonance frequencies of water and of fat with regard to the set strength of the basic magnetic field B0.

The first refocusing pulse 36 framed by spoiler gradients 38 serves to bring the spins of the predetermined volume segment into a steady state. The readout of the MR data for one line of k-space along the x-direction respectively takes place after a refocusing pulse 36 and is switched directly after the first phase coding gradient $G_y$ and the second phase coding gradient $G_{z2}$, wherein the frequency gradient $G_x$ is switched during the readout of the frequency coding gradient $G_x$.

Figure 3:
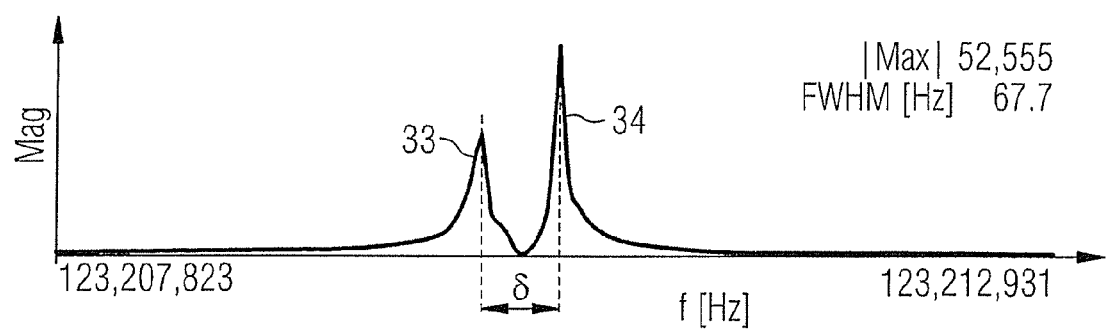
FIG. 3 illustrates the chemical shift between water and fat.

The chemical shift δ between water and fat (which amounts to 3.5 ppm) is shown in FIG. 3. This means that, given a strength of the magnetic field $B_0$ of 1.5 T, the frequency difference δ or chemical shift δ between the resonance frequency 34 or water protons and the resonance frequency 33 of fat protons amounts to 220 Hz.

Figure 4:
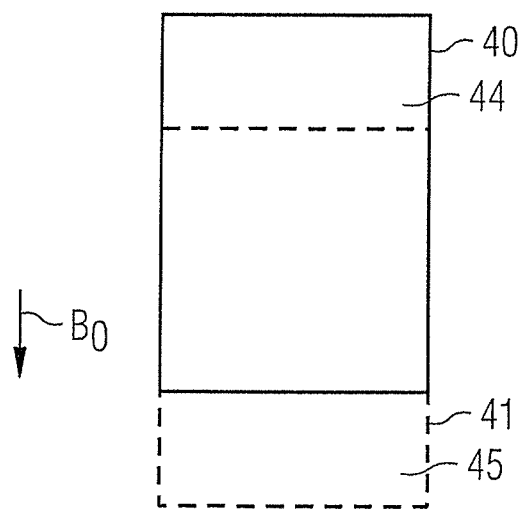
FIG. 4 shows a volume excited with regard to water in comparison to a volume excited with regard to fat according to the prior art.
Figure 5:
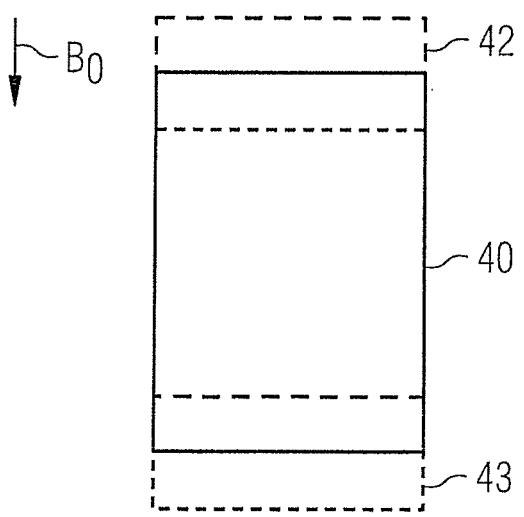
FIG. 5 shows a target volume according to the invention in comparison to a volume excited with regard to water and a volume excited with regard to fat.

The present invention will be explained in detail with the use of FIGS. 4 and 5.

According to the prior art, the frequency range of the RF excitation pulse 37 is set corresponding to the resonance frequency of water, such that according to the prior art the target volume 40 corresponds to that volume in which the water protons are excited. Due to the chemical shift, such an RF excitation pulse 37 set with regard to fat excites a volume 41 which has the same dimensions as the volume 40 but is shifted by approximately 30% in the direction of the basic magnetic field $B_0$ relative to this target volume.

Due to this shift, no fat protons are excited in the upper volume segment 44 of the target volume 40 (which is not a component of the volume 41), which leads to dark regions ("dark bands") in the generated MR image data set. On the other hand, fat protons are excited in the lower volume segment 45 of the volume 41 (which does not belong to the target volume 40), which leads to aliasing artifacts in the lower region of the target volume 40.

According to the invention, the center frequency of the frequency range of the RF excitation pulse 37 is now set to the frequency which lies in the center between the resonance frequency 34 of water and the resonance frequency 33 of fat. For example, the center frequency (and therefore the frequency range of the RF excitation pulse 37) is decreased by 110 Hz relative to the prior art.

Although the volume 42 in which the water protons are excited is thereby shifted slightly relative to the target volume 40, counter to the direction of the basic magnetic field $B_0$ (upward in FIG. 5), the shift of the volume 43 in which the fat protons are excited amounts to only half relative to the prior art, whereby the dark region ("dark band") is halved relative to the prior art.

According to the invention, the acquisition of the MR data occurs in the target volume 40. In other words, the two phase coding gradients $G_y$, $G_{z2}$ and the frequency coding gradient $G_x$ are set such that the target volume 40 is scanned. Expressed in a different way, according to the invention the predetermined volume segment (the target volume 40) corresponds to neither the volume 42 in which the water protons are excited nor the volume 43 in which the fat protons are excited.

So that the volume 42 or the volume 43 includes the entire target volume 40, the strength of the selection gradient $G_{z1}$ can be decreased such that the volume 42 extends just up to the lower boundary (see FIG. 5) of the target volume 40 and such that the volume 43 extends just to the upper limit of the target boundary of the target volume 40. Via this procedure, the dark regions can be nearly completely avoided in the MR image data set of the target volume 40 that is to be created.

Moreover, the scanning of the measurement signals in the MR data acquisition can take place with a higher frequency than would be necessary according to the Nyquist theorem in order to acquire the MR data within the target volume 40, which is also known as oversampling. In addition to the target volume 40, regions above and below (see FIG. 5) the target volume 40 are acquired by this oversampling in addition to the target volume 40. An MR image data set of the volume enlarged by the oversampling relative to the target volume 40 is subsequently created, and the MR image data set of the target volume 40 is extracted from this MR image data set of the enlarged volume, whereby the aliasing artifacts are essentially eliminated.

Figure 6:
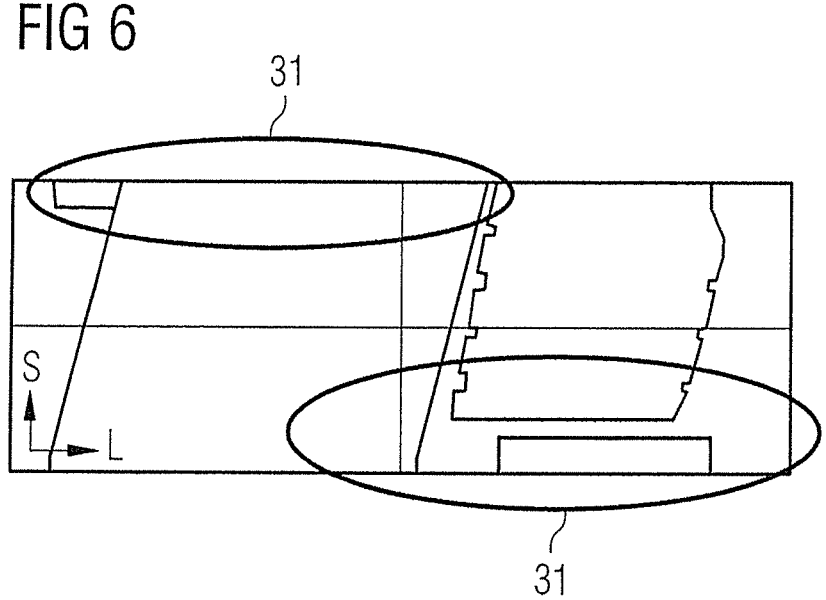
FIG. 6 illustrates aliasing artifacts for an MR method according to the prior art, given a phantom example.
Figure 7:
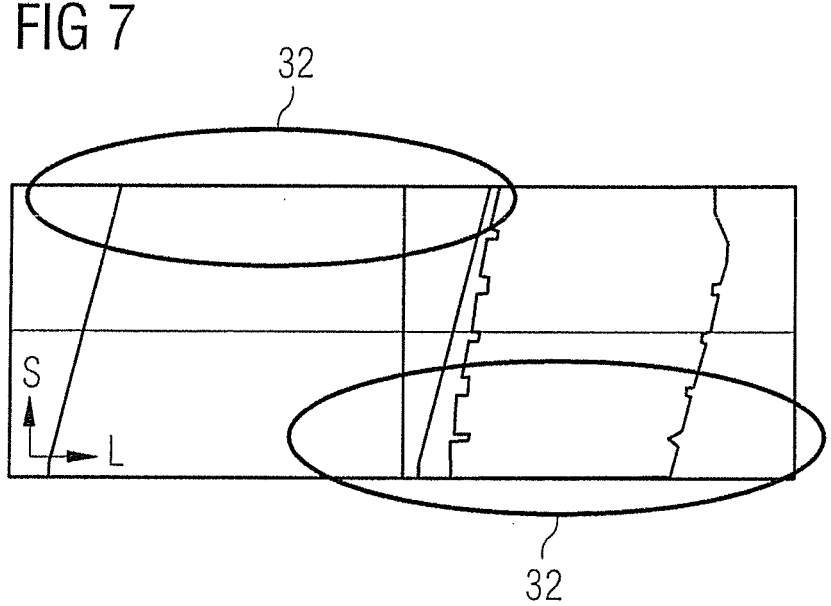
FIG. 7 illustrates aliasing artifacts for an MR method according to the invention given the same phantom example as in FIG. 6.

Results of the present invention in comparison to the prior art are shown with FIGS. 6 and 7.

While an MR image of a phantom for an MR method according to the prior art (in which the center frequency of the frequency range of the RF excitation pulse corresponds to the resonance frequency of water) is shown in FIG. 6, FIG. 7 shows an MR image which was generated via a method according to the invention, wherein the center frequency of the frequency range of the RF excitation pulse was set precisely in the center between the resonance frequency of water and the resonance frequency of fat. It is apparent that the artifacts 31 are clearly apparent in the MR image according to the prior art in FIG. 6, while nearly no artifacts are apparent in the MR image in FIG. 7, created according to the invention.

FIG. 8 shows a flow chart of a method according to the invention.

In the first Step S1 the resonance frequencies of fat and water are determined depending on the strength of the basic magnetic field $B_0$ of the magnetic resonance system.

In the following Step S2 the center frequency of the RF excitation pulses is set such that it lies between the resonance frequency of fat and the resonance frequency of water.

In Step S3 the MR data of the predetermined volume segment are subsequently acquired with the pulse sequence shown in FIG. 2, for example.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to acquire magnetic resonance (MR) data comprising:

from a computerized control unit, operating an MR data acquisition unit with an examination subject therein to acquire MR data from a predetermined three-dimensional volume segment of the examination subject by selectively exciting nuclear spins in said three-dimensional volume segment with a radio frequency (RF) excitation pulse while simultaneously activating a first magnetic field gradient, two second magnetic field gradients, and a third magnetic field gradient;

acquiring said MR data from the three-dimensional volume segment of the examination subject, resulting from the excited nuclear spins, with phase coding by said two second magnetic field gradients and spatial coding by said third magnetic field gradient; and in said computerized control unit, setting a frequency range of said RF excitation pulse dependent on respective resonant frequencies of at least two types of said nuclear spins in said three-dimensional volume segment, to cause a center frequency of said frequency range to be between said respective resonance frequencies by calculating an average of said resonance frequencies of said at least two types of nuclear spins, and setting said center frequency to be equal to said average.

2. A method as claimed in claim 1 wherein said two types of nuclear spins to be acquired are water and fat, and comprising setting said center frequency to a frequency midway between the resonance frequency of water and the resonance frequency of fat.

3. A method as claimed in claim 1 comprising frequency encoding said MR signal with said third magnetic field gradient, entering said MR data into k-space for which said third magnetic field gradient represents an access defining lines in k-space in which said MR data are entered, and comprising reading out MR data in a direction of said third magnetic field gradient in one step that comprise one line of k-space.

4. A method as claimed in claim 1 comprising operating said MR data acquisition unit to set a strength of said first magnetic field gradient to be lower to cause respective border regions before and after said volume segment in a direction of said first magnetic field gradient to be excited and acquiring MR data from the respective border regions.

5. A method as claimed in claim 4 comprising acquiring MR data from respective border regions before and after said volume segment in a direction of said first magnetic field gradient, by oversampling.

6. A method as claimed in claim 1 comprising, before acquiring said MR data, activating a selective refocusing pulse in a frequency range corresponding to said frequency range of said RF excitation pulse.

7. A method to acquire magnetic resonance (MR) data comprising:

from a computerized control unit, operating an MR data acquisition unit with an examination subject therein to acquire MR data from a predetermined three-dimensional volume segment of the examination subject by selectively exciting nuclear spins in said three-dimensional volume segment with a radio frequency (RF) excitation pulse while simultaneously activating a first magnetic field gradient, two second magnetic field gradients, and a third magnetic field gradient;

acquiring said MR data from the three-dimensional volume segment of the examination subject, resulting from the excited nuclear spins, with phase coding by said two second magnetic field gradients and spatial curving by said third magnetic field gradient;

operating said MR data acquisition unit during acquisition of said MR data to generate a basic magnetic field, in a basic magnetic field direction, in which the examination subject is located, generating said first magnetic field gradient in said basic magnetic field direction;

generating a first of said two second magnetic field gradients as a phase encoding gradient in said basic magnetic field direction;

generating said third magnetic field gradient perpendicularly to said basic magnetic field direction;

generating a second of said two second magnetic field gradients as a phase encoding gradient perpendicularly to the direction of said first of said two second magnetic field gradients and said third magnetic field gradient; and setting a frequency range of said RF excitation pulse dependent on respective resonant frequencies of at least two types of said nuclear spins in said three-dimensional volume segment, to cause a center frequency of said frequency range to be between said respective resonance frequencies.

8. A magnetic resonance apparatus to acquire magnetic resonance (MR) data comprising:

an MR data acquisition unit;

a control unit configured to operate said an MR data acquisition unit with an examination subject therein to acquire MR data from a predetermined three-dimensional volume segment of the examination subject by selectively exciting nuclear spins in said three-dimensional volume segment with a radio frequency (RF) excitation pulse while simultaneously activating a first magnetic field gradient, two second magnetic field gradients, and a third magnetic field gradient;

said control unit being configured to acquire MR data from the three-dimensional volume segment of the examination subject, resulting from the excited nuclear spins, with phase coding by said two second magnetic field gradients and spatial coding by said third magnetic field gradient; and said control unit being configured to set a frequency range of said RF excitation pulse dependent on respective resonant frequencies of at least two types of said nuclear spins in said three-dimensional volume segment, to cause a center frequency of said frequency range to be between said respective resonance frequencies, and to calculate an average of said resonance frequencies of said at least two types of nuclear spins, and to set said center frequency to be equal to said average.

9. A non-transitory, computer-readable data storage medium encoded with programming instructions, said data storage medium being loaded into a computerized control unit of a magnetic resonance (MR) apparatus comprising an MR data acquisition unit, and said programming instructions causing said computerized control unit to:

operate said MR data acquisition unit with an examination subject therein to acquire MR data from a predetermined three-dimensional volume segment of the examination subject by selectively exciting nuclear spins in said three-dimensional volume segment with a radio frequency (RF) excitation pulse while simultaneously activating a first magnetic field gradient, two second magnetic field gradients, and a third magnetic field gradient;

acquire MR data from the three-dimensional volume segment of the examination subject, resulting from the excited nuclear spins, with phase coding by said two second magnetic field gradients and spatial coding by said third magnetic field gradient; and set a frequency range of said RF excitation pulse dependent on respective resonant frequencies of at least two types of said nuclear spins in said three-dimensional volume segment, to cause a center frequency of said frequency range to be between said respective resonance frequencies, and calculate an average of said resonance frequencies of said at least two types of nuclear spins, and set said center frequency to be equal to said average.

10. A magnetic resonance apparatus to acquire magnetic resonance (MR) data comprising:

an MR data acquisition unit comprising a basic field magnet that generates a basic magnetic field, in a basic magnetic field direction, in which an examination subject is situated;

a computerized control unit configured to operate the MR data acquisition unit to acquire MR data from a predetermined three dimensional volume segment of the examination subject by selectively exciting nuclear spins in said three-dimensional volume segment with a radio-frequency (RF) excitation pulse while simultaneously activating a first magnetic field gradient, to second magnetic field gradients, and a third magnetic field gradient;

said computerized control unit being configured to operate said MR data acquisition unit to acquire said MR data as signals resulting from the excited nuclear spins, with said first magnetic field gradient activated in said basic field direction, a first of said two second magnetic field gradients being activated as a phase encoding gradient in said basic field direction, said third magnetic field gradient being activated as a spatial encoding gradient perpendicularly to said basic magnetic field direction, and a second of said two second magnetic field gradients being activated as a phase coding gradient perpendicularly to the direction of the first of said two second magnetic field gradients and said third magnetic field gradient; and said computerized control unit being configured to set a frequency range of said RF excitation pulse dependent on respective resonant frequencies of at least two types of said nuclear spins in said three-dimensional volume segment, to cause a center frequency of said frequency range to be between said respective resonance frequencies.

11. A non-transitory, computer-readable data storage medium encoded with programming instructions, said data storage medium being loaded into a computerized control and processing unit of a magnetic resonance (MR) apparatus comprising an MR data acquisition unit that includes a basic field magnet that generates a basic magnetic field in a basic magnetic field direction, said programming instructions causing said computerized control and processing unit to:

operate said MR data acquisition unit with an examination subject situated therein to acquire MR data from a predetermined three-dimensional volume segment of the examination subject by selectively exciting nuclear spins in said three-dimensional volume segment with a radio-frequency (RF) excitation pulse while simultaneously activating a first magnetic field gradient, to second magnetic field gradients, and a third magnetic field gradient, said acquired MR data resulting from the excited nuclear spins;

operate said MR data acquisition unit during acquisition of said MR data to activate a first of said two second magnetic field gradients as a phase encoding gradient in said basic magnetic field direction;

operate said MR data acquisition unit during acquisition of said MR data to activate said third magnetic field gradient as a spatial coding gradient perpendicularly to said basic magnetic field direction;

operate said MR data acquisition unit during acquisition of said MR data to activate a second of said two magnetic field gradients as a phase encoding gradient perpendicularly to the direction of said first of said two second magnetic field gradients and said third magnetic field gradient; and set a frequency range of said RF excitation pulse dependent on respective resonant frequencies of at least two types of said nuclear spins in said three-dimensional volume segment, to cause a center frequency of said frequency range to be between said respective resonance frequencies.

\* \* \* \* \*